US007994217B2

(12) United States Patent
Nidamarty et al.

(10) Patent No.: US 7,994,217 B2
(45) Date of Patent: Aug. 9, 2011

(54) PRENATAL MULTIVITAMIN/MULTIMINERAL SUPPLEMENT

(75) Inventors: Prasad Nidamarty, Miamisburg, OH (US); William R. Hurd, Noblesville, IN (US); Roland J. Bydlon, Indianapolis, IN (US); William C. Williams, Indianapolis, IN (US); Michael Dempsey, Columbus, IN (US); Amy Erbskorn, Dublin, OH (US)

(73) Assignee: Xanodyne Pharmaceuticals, Inc., Newport, KY (US)

( * ) Notice: Subject to any disclaimer, the term of this patent is extended or adjusted under 35 U.S.C. 154(b) by 247 days.

(21) Appl. No.: 10/375,600

(22) Filed: Feb. 27, 2003

(65) Prior Publication Data
US 2003/0206969 A1 Nov. 6, 2003

(51) Int. Cl.
*A61K 31/295* (2006.01)
*A61K 31/00* (2006.01)
*A61K 33/06* (2006.01)
*A61K 33/26* (2006.01)
*A61K 33/30* (2006.01)
*A61K 33/34* (2006.01)
*A61P 3/02* (2006.01)

(52) U.S. Cl. ........ 514/502; 424/630; 424/641; 424/643; 424/646; 424/648; 424/682; 424/DIG. 6; 514/52; 514/167; 514/249; 514/251; 514/276; 514/351; 514/355; 514/458; 514/474; 514/566; 514/567; 514/702; 514/904; 514/905

(58) Field of Classification Search ............... 424/400, 424/441, 451, 464, 468, 470, 489, 499, 502
See application file for complete search history.

(56) References Cited

U.S. PATENT DOCUMENTS

| | | | | |
|---|---|---|---|---|
| 3,969,540 A | 7/1976 | Jensen | | 426/657 |
| 4,167,564 A | 9/1979 | Jensen | | 424/177 |
| 4,183,947 A | 1/1980 | Cockerill | | 424/295 |
| 4,431,634 A * | 2/1984 | Ellenbogen | | 424/648 |
| 4,599,152 A | 7/1986 | Ashmead | | 204/72 |
| 4,725,427 A | 2/1988 | Ashmead et al. | | 424/44 |
| 4,774,089 A | 9/1988 | Ashmead | | 424/157 |
| 4,830,716 A | 5/1989 | Ashmead | | 204/72 |
| 4,863,898 A | 9/1989 | Ashmead et al. | | 514/6 |
| 5,292,538 A | 3/1994 | Paul et al. | | 426/74 |
| 5,292,729 A | 3/1994 | Ashmead | | 514/168 |
| 5,494,678 A | 2/1996 | Paradisses et al. | | 424/439 |
| 5,516,925 A | 5/1996 | Pedersen et al. | | 556/50 |
| 5,596,016 A | 1/1997 | Ashmead et al. | | 514/492 |
| 5,882,685 A | 3/1999 | Ashmead | | 424/617 |
| 5,888,553 A | 3/1999 | Grant et al. | | 424/655 |
| 5,888,563 A | 3/1999 | Mechansho et al. | | 426/72 |
| 4,830,716 A | 12/1999 | Ashmead | | 205/457 |
| 6,114,379 A | 9/2000 | Wheelwright et al. | | 514/92 |
| 6,159,530 A | 12/2000 | Christiansen et al. | | 426/656 |
| 6,166,071 A | 12/2000 | Ashmead et al. | | 514/494 |
| 6,207,204 B1 | 3/2001 | Christiansen et al. | | 426/74 |
| 6,299,896 B1 | 10/2001 | Cooper et al. | | 424/441 |
| 6,358,544 B1 * | 3/2002 | Henry et al. | | 426/74 |
| 6,413,558 B1 * | 7/2002 | Weber et al. | | 426/2 |
| 6,495,177 B1 * | 12/2002 | deVries et al. | | 426/72 |
| 6,521,247 B1 * | 2/2003 | deVries | | 424/439 |
| 6,579,544 B1 * | 6/2003 | Rosenberg et al. | | 424/736 |

FOREIGN PATENT DOCUMENTS

| | | |
|---|---|---|
| GB | 1 224 589 | 3/1971 |
| GB | 2 168 354 | 6/1986 |
| WO | WO 02 30948 | 4/2002 |
| WO | WO 03003981 A2 * | 1/2003 |

OTHER PUBLICATIONS

Hallberg, L. et al., "Low bioavailability of carbonyl iron in man: studies on iron fortification of wheat flour", Jan. 1987, The American Journal of Clinical Nutrition, 43, pp. 59-67.*
Jeppsen et al., Safety Evaluation of Ferrous Bisglycinate Chelate, Food and Chemical Toxicalogy (1999), pp. 723-731.*
Internet Document [URL:HTTP://www.iherb.com/advferrochel.html], *Advanced Ferrochel*, Retrieved on Jul. 30, 2003.
Internet Document [URL:HTTP://www.herbsmd.com/shop/xq/asp/pid.18564/qx/productdetail.html], *Advanced Iron Ferrochel*, Retrieved on Jul. 30, 2003.
Internet Document [URL:HTTP://www.albionlabs.com/human/ferrochel.htm], *Ferrochel*, Retrieved on Jul. 30, 2003.
H. DeWayne Ashmead, Ph.D., *Comparative Intestinal and Subsenquent Metabolism of Metal Amino Acid Chelates and Inorganic Metal Salts*, of Subramanian, K.S. et al., Biological and Trace Element research, American Chemical Society, Washington, D.C., pp. 306-319, 1991.
Coptin, et al, *Tolerability of Iron: A Comparison of Bis-Glycino Iron II and Ferrous Sulfate*, Clinical Therapeutics, vol. 13, No. 5, 1991.
Dawson, Earl B., et al., *Bioavallability of Iron in Two Prenatal Multivitamin/Multimineral Supplements*, The Journal of Reproductive Medicine, 45:5 (2000), pp. 403-409.
Jeppsen, et al., *Safety Evaluation of Ferrous Bisglycinate Chelate*, Food and Chemical Toxicology 37(1999) 723-731.

(Continued)

*Primary Examiner* — Johann Richter
*Assistant Examiner* — Frank Choi
(74) *Attorney, Agent, or Firm* — Wood, Herron & Evans, LLP

(57) ABSTRACT

Multivitamin/Multimineral supplements are provided for supplementing iron and desirable nutrients in the diet of mammals. The supplements include an iron-amino acid chelate, a form of iron more bioavailable than traditional iron salts. The supplements may further include a pharmaceutically accepted salt form of iron as well as other nutritional vitamins and minerals. The supplements are useful for providing iron for pregnant and lactating females as well as for persons suffering from anemia.

36 Claims, No Drawings

OTHER PUBLICATIONS

W.H. Kirchhoff, *The Treatment of Iron Deficiency Anemia with Iron Chelate Tablets*, Therapiewoche (Germany, West), 1983, 33/37 (4833-4842).

Pineda, et al., *Effectiveness of Iron Amino Acid Chelate on the Treatment of Iron Deficiency Anemia in Adolescents*, J. of Applied Nutrition, vol. 46, Nos. 1&2, 1994.

Iost et al., *Reeiprolenting Hemoglobin in Iron Deficiency Anemia in Young Children through Liquid Milk Fortification with Bioavailable Iron Amino Acid Chelate*, Journal of American College of Nutrition vol. 17, No. 2 1998.

Internet Document [URL:HTTP://www.herbtrader.com/200392.html], *Iron Ferrochel Liquid by Natrol*, Retrieved Jul. 30, 2003.

Internet Document [URL:HTTP://www.em.infinity2.info/product/pdf/9060.pdf], *Prenatal Formula. Nutrition During Pregnancy*, Retrieved Jul. 30, 2003.

Pineda, et al., *Effectiveness of Treatment of Iron-Deficiency Anemia in Infants and Young Children With Ferrous Bis-glycinate Chelate*, Nutrition 17:381-384, 2001.

Schuette, et al, *Comparison of Tolerability Between Bisglycino-iron and Ferrous Sulfate in Normal Premenopausal Women*, Final Report to Albion Laboratories, Inc., University of Chicago, 1989.

Szarfarc, et al., *Relative effectiveness of iron bis-glycinate chelate (Ferrochel) and ferrous sulrface in the control of iron dificiency in pregnant women*, Archivos Lationamericanos de Nutricion Suplemento Vo. 51, No. 1, 2001.

Internet Document [URL:HTTP://www.stuartnatal.com/duet/duet_tablets.html], *The Duet Difference*, Retrieved on Jul. 31, 2003.

International Search Report for PCT/US03/13663, mailed Dec. 8, 2003.

* cited by examiner

PRENATAL MULTIVITAMIN/MULTIMINERAL SUPPLEMENT

BACKGROUND OF THE INVENTION

I. Field of the Invention

The present invention relates generally to a composition for a multivitamin/multimineral supplement and more specifically, to a composition useful as a prenatal iron supplement.

II. Description of the Prior Art

Iron is needed for the production of red blood cells and for a healthy circulatory system used to deliver nutrients and energy to muscles, organs, and other bodily tissue for maintaining a strong and healthy body. Particularly, iron occupies a central position in hemoglobin synthesis and erythropoiesis. An iron deficiency generally interferes with this process and, in time, often leads to anemia. The signs and symptoms of iron deficiency are generally attributable to the anemia it produces. Symptoms include weakness, fatigue, dizziness, heart palpitations, nausea, anorexia, constipation and menstrual irregularities. In the United States, it is estimated that about 2% of the men and more than about 15% of the women of child bearing age are deficient in iron. For example, a study estimated that about 38% of women of child bearing age in San Diego are iron deficient. It is therefore desirable to provide an iron supplement for reducing iron deficiency.

Blood loss is the most common cause of iron deficiency in adults. The high deficiency of iron in women is due to the obligatory blood loss of each menstrual cycle. Bleeding from the gastrointestinal tract (for example, because of peptic ulcer, diverticulosos, or malignancy) is the primary cause of iron deficiency in men. Impaired absorption of iron following total or partial gastrectomy and in patients with chronic diarrhea and/or malabsorption may also cause depletion of iron reserves. Increased demand for iron in infants, young children, adolescents, and adults may also lead to an iron-deficiency state. Lifestyle changes resulting from increased workloads, exercise, and/or routine physical activity for example, cause bodily changes generally leading to an increase in the demand for iron. For example, pregnancy generally increases the demands for iron in a woman's body. Particularly, during the second half of pregnancy, the demands for iron are significant. The increased demand for iron is frequently compounded by inadequate intake of iron because of an iron poor diet. It is therefore desirable to provide an iron supplement for addressing iron deficiency, anemia, and the increase in demands for iron.

Further related to pregnancy, a supplement of iron is important because many health problems with the mother and/or fetus may be associated with an inadequate amount of dietary iron. For example, anemia during pregnancy is associated with a significant increase in maternal mortality. Particularly, anemia in the third trimester can be dangerous if left untreated. Statistically, up to about 20% of all pregnant women suffer from anemia. Generally, as the pregnancy progresses, the demands for iron rise and, in many cases, these growing demands cannot be met by either the iron provided in a mother's normal diet or by her body's own iron reserves. Accordingly, iron supplementation is needed throughout the term of a pregnancy and for as long as a woman is lactating.

To address anemia as well as the increasing demands of iron, it has been recommended that a supplementation of iron be given to ensure that approximately 3 mg of iron is absorbed into the body per day. The prior art has provided supplementation of iron for the body through the use of caplets, tablets, soft/hard shell capsules, and suspensions including an iron salt. There are many iron salts included in supplements, such as ferric salts ($Fe^{3+}$), ferrous salts ($Fe^{2+}$) and carbonyl iron. Examples of ferrous iron salts include ferrous sulfate and ferrous fumarate The use of iron salts, as with most metal salts, however, generally presents weaknesses and drawbacks. When supplements including commonly used ferric ($Fe^{3+}$) salts (also referred to as iron (III) salts) are ingested and exposed to gastric juices having an acidic pH of between 1 and 3 in the stomach, the ferric iron ($Fe^{3+}$) is converted to ferrous iron ($Fe^{2+}$). It is this ferrous state of the iron that is most absorbed by the small intestine. However, conversion of the ferric iron ($Fe^{3+}$) to the ferrous iron ($Fe^{2+}$) form causes gastric upset and abdominal pain. In fact, a large percentage of patients that consume common iron salts complain of gastrointestinal tract upset. Further, such conversion results in a small, unsatisfactory percentage of the total iron in the supplement being absorbed. It would, therefore, be desirable to have a supplement wherein the iron is absorbed without an accompanying gastrointestinal upset and discomfort.

Further, organic or inorganic salt forms of iron are difficult to absorb in the human body and, therefore, are needed in large amounts to satisfy the daily iron requirements and the increase in iron demand. More specifically, following ingestion and ionization of an iron salt, such as ferrous sulfate ($FeSO_4$), it is eventually transported to the small intestine where the majority of absorption takes place. Generally, absorption begins in the duodenum in a mildly acidic fluid environment (pH of about 5-6), and is maximal in the upper jejunum where the fluid is mildly basic (pH of about 7-8). The intestinal walls possess charges on the luminal surface that present a challenge for the passage or absorption of positively charged cationic metal species ($Fe^{2+}$) to pass through the intestinal wall. These charges, however, allow the negatively charged anionic counter ion species ($SO_4^{-2}$) to pass through the intestinal membrane. Thus, most of the vital metal (positive cationic metal) is generally excreted from the body through the intestinal tract while the absorbed anions are cleared hepatically and exit the body in the urine. Such metabolic pathways are further discussed in Kirchoff, H. W. "*The Treatment of Iron Deficiency Anemia with Iron Chelate Tablets*", Therapiewoche 33(37), 4833-4842, 1983, the disclosure of which is herein incorporated by reference in its entirety.

Efforts have been made to increase the absorption and decrease the clearance of iron by the body. More specifically, increasing the concentration of the iron in salt forms utilizing organic or inorganic carriers associated with the iron have produced only limited success and have drawbacks associated therewith. For example, ferrous sulfate is the most widely used form of iron supplementation, particularly for pregnant and lactating females, and for treating various forms of iron deficiency anemia, as described in Schuette, S., et al., "*Comparison of Tolerability between Bisglycino-iron and Ferrous Sulfate in Normal Premenopausal Women*", Final Report to Albion Labs, University of Chicago, 1989, the disclosure of which is herein incorporated by reference in its entirety. However, while ferrous sulfate is absorbed into the blood stream and is widely prescribed, it too is sometimes not very well tolerated and produces abdominal discomfort and changes in bowel habits. This adversely affects treatment compliance in that patients frequently complain about gastric side effects such as diarrhea, constipation, abdominal pain, and nausea. Many times, this discomfort is the primary reason that a patient will stop taking a prescribed regimen. Thus, more tolerable forms of iron therapy would be desirable.

Further, patients may stop taking an iron-containing supplement as part of a prescribed regimen because the size of the supplement may be too large and, therefore, uncomfortable or difficult to swallow. Particularly, with respect to iron, due to the gastric conversion, low absorption, and high clearance rates of prior art forms of iron, large quantities of the iron need to be ingested in order to achieve the absorption of the recommended 3 mg of iron per day. In addition, the supplement itself may have a bad after taste. This is particularly true for expectant mothers, because upon becoming pregnant, the woman's sense of taste and smell and her ability to swallow certain foods changes. This often makes it difficult for a pregnant woman to maintain a regimen of ingesting prescribed supplements containing iron salts. Additionally, pregnant women generally consider a prenatal vitamin to be large and hard to swallow. For this reason, many women do not take prenatal vitamins according to the regimen their health care providers have prescribed or recommended.

As a result of the above drawbacks, many humans fail to take iron supplements as part of a required regimen. Consequently, iron levels often fall below those recommended, and the person may become anemic. Particularly, pregnant and lactating females failing to take prenatal vitamins as required may not get the nutrition that they and their developing fetus require. Consequently, many problems may arise with the pregnancy and/or with the child, up to and including mortality.

Thus, it would be desirable to provide a composition to supplement iron in a diet while avoiding deleterious side effects in the gastrointestinal tract. It would also be desirable to provide such a composition in a suitable dosage form, such as a tablet, containing iron in a form highly absorbed into the blood. It would be further desirable to reduce the size of the composition in order to facilitate adherence to a dosage regimen. To this end, it would be still further desirable that the regimen be satisfied by ingesting a single tablet once or only a few times per day. Compliance with a prenatal multivitamin/multimineral supplement is optimized with a once-a-day dosage. Finally, it would be desirable to accomplish the above while maintaining iron levels in pregnant females, particularly those suffering from anemia and/or in their third trimester, and lactating females at medically desirable levels.

SUMMARY OF THE INVENTION

The present invention addresses the problems associated with the prior art supplements containing iron and reduces or eliminates their weaknesses and drawbacks previously described. In doing so, the present invention provides a composition including a bioavailable source of iron in the form of an iron-amino acid chelate, such as ferrous bis-glycinate chelate, which may be combined with a more concentrated pharmaceutically acceptable salt form of iron, such as ferrous fumarate, in a single dosage form, such as a pill, a tablet, a caplet, or a capsule. Both ferrous bis-glycinate chelate and ferrous fumarate reduce the gastrointestinal side effects caused by other commonly used iron salts. The present compositions are useful for supplementing iron to mammals in general, and in particular to pregnant and lactating females.

Inclusion of an iron-amino acid chelate as a source of iron provides many benefits. The iron-amino acid chelate is a coordinated complex wherein the iron atom is coordinated with one or more amino acids or peptides. By virtue of the coordinated nature of iron-amino acid chelate, the iron atom in the chelate is chemically neutral and not ionized or charged. To this end, the iron is more readily absorbed through the intestinal wall and into the blood stream. In one embodiment of the present invention, the iron-amino acid chelate is ferrous bis-glycinate chelate. One form of ferrous bis-glycinate chelate is commercially available from Albion Laboratories, Inc., of Clearfield, Utah, and sold under the trade name of Ferrochel®.

Ferrous bis-glycinate chelate generally has greater bioavailability relative to other conventional forms of iron. In addition, ferrous bis-glycinate chelate is stable, further contributing to its beneficial bioavailability properties. Further, ferrous bis-glycinate chelate presents fewer side effects than more commonly used iron salts, such as ferrous sulfate. The increased bioavailability and reduced side effects makes ferrous bis-glycinate chelate particularly attractive for inclusion in iron supplements, particularly those directed to pregnant females and especially to pregnant females in their third trimester and/or suffering from anemia. Moreover, the high oral bioavailability of ferrous bis-glycinate chelate allows the dosage amount to be generally smaller than prior art forms of iron. Consequently, the present composition may be small relative to the size of prior art supplements. Thus, the present invention provides compositions which are easier to swallow and more likely to be ingested.

In one aspect of the present invention, a combination of ferrous bis-glycinate chelate and ferrous fumarate is present in a pharmaceutically acceptable formulation to deliver elemental iron to a mammal in a single dosage. Generally, in order to properly supplement dietary iron to the recommended daily allowance of 3 mg, a once-a-day dosage of at least approximately 20 mg of a suitable form of iron is needed. Ferrous bis-glycinate chelate is approximately 20% elemental iron, whereas ferrous fumarate is approximately 33% elemental iron. By combining ferrous bis-glycinate chelate and ferrous fumarate in a single composition, a higher percentage of iron can be absorbed into the blood circulation with a corresponding reduction in the total weight and volume of the iron, and as a result, a reduction in the overall size of the dosage form. Thus, a combination of ferrous fumarate and ferrous bis-glycinate chelate in a composition may provide the iron supplementation needed by iron deficient patients as well as pregnant or lactating women in a small sized tablet without deleterious gastrointestinal side effects. To this end, this combination is useful as a pre-natal tablet for administration to pregnant or lactating females. Further, a smaller dosage size increases the likelihood of patient compliance with a regimen. In another aspect, the combination further includes vitamins and minerals to form a multivitamin/multimineral supplement. In yet another aspect of the present invention, ferrous bis-glycinate chelate is combined with folic acid in a suitable formulation and used to treat anemia in pregnant females, particularly pregnant females in the third trimester.

These and other benefits and advantages of the composition of the present invention shall be apparent to persons of ordinary skill in the art with reference to the following detailed description of the invention.

DETAILED DESCRIPTION OF THE INVENTION

The present invention provides compositions including a bioavailable form of iron in an iron-amino acid chelate, in a single pharmaceutically acceptable dosage form, such as a pill, a tablet, a caplet, or a capsule, suitable for ingestion. The iron-amino acid chelate may be combined with a more concentrated, pharmaceutically acceptable salt form of iron, such as a ferrous iron salt ($Fe^{2+}$). In one embodiment of the present invention, the composition includes a combination of ferrous bis-glycinate chelate as an iron-amino acid chelate and ferrous fumarate as a pharmaceutically acceptable salt form of iron. Ferrous bis-glycinate chelate generally has greater bioavailability than previously disclosed iron salts. Also, both ferrous bis-glycinate chelate and ferrous fumarate alleviate the gastrointestinal side effects often present when using other common iron salts, as described in Schuett, Sally et al., *Comparison of Tolerability Between Bisglycino-iron and Ferrous Sulfate in Normal Premenopausal Women*, Final Report to Albion Laboratories, University of Chicago, 1989; Dawson, Earl B., et al., *Bioavailability of Iron in Two Prenatal Multivitamin/Multimineral Supplements*, The Journal of Reproductive Medicine, Vol. 45, No. 5, May 2000, pp. 403-409; and Coplin, Maggie et al., *Tolerability of Iron: A Comparison of Bis-Glycino Iron II and Ferrous Sulfate*, Clinical Therapeutics, Vol. 13, No. 5, 1991, the disclosures of which are herein incorporated by reference in their entireties. The high bioavailable properties of the iron-amino acid chelate in compositions of the present invention allows for a lower overall iron dosage and a smaller composition relative to the iron supplements of the prior art. This generally results in improved patient compliance with a dosage regimen.

The iron-amino acid chelate is more generally a metal-ligand chelate. A metal-ligand chelate is typically formed from the reaction of a metal or a metal ion in the form of a metal salt with one or more reactive ligands. The chelate will generally have a metal:ligand mole ratio of 1:1-3 depending on the metal and ligand in question and its valence or particular oxidation state. In one embodiment of the present invention, the metal:ligand mole ration is 1:2. The metal-ligand chelate is a complex or coordination compound comprising a metal ion associated with one or more ligands, such as amino acids, via electron donating groups on each ligand. The term "chelate" also refers to the mode of association between the metal and the ligand(s) and generally includes covalent bonds and ionic associations. Chelates comprising coordinate covalent bonds between the metal and the ligand are typically inert and uncharged. When a single electron donor ligand containing two or more donor groups is chelated to a single metal atom, the ligand is generally referred to as a polydentate ligand. For example, a bidentate ligand has two donor groups chelated to a single metal atom. Suitable ligands for metals include, without limitation, natural and unnatural amino acids, such as alanine, arginine, asparagine, aspartic acid, cysteine, cystine, glutamine, glutamic acid, glycine, histidine, hydroxyproline, isoleucine, lysine, leucine, methionine, ornithine, phenylalanine, proline, serine, threonine, tryptophan, tyrosine, and valine. Suitable ligands also include combinations of the amino acids, such as in the form of dipeptides, tripeptides, quadrapeptides, or polypeptides for example. Amino acid ligands may chelate with a metal atom to form a sterically permissible four, five, and sometimes six-membered ring structure and neutralize the positive charge of the metal by the electron pairs available on the carboxylic acid and/or the amine functional groups. At least two and sometimes three amino acids can be bound to a single metal atom, depending on its oxidative state, to form a bicyclic and/or tricyclic ringed complex. A metal atom, such as iron, covalently bound to one or more amino acid ligands is chemically inert and may more easily be absorbed through the small intestine into the circulatory system.

The term "iron-amino acid chelate", as used herein, is intended to refer to iron complexes comprising at least one iron atom chelated to one or more amino acid ligands in a manner described above. Iron-amino acid chelates generally have greater bioavailability than other forms of iron by virtue of a chemically inert iron and enhanced absorption of the chelate through the intestinal wall due to a reduced or absence of charge interference. Suitable iron-amino acid chelates for the present invention include, for example, ferrous bis-glycinate chelate.

Ferrous bis-glycinate chelate is an iron complex having a single polyvalent cationic iron atom bound to lone electron pairs of the amine and carboxylic acid functional groups of two glycine ligands. Each glycine molecule forms a five-membered ring with the iron atom. Structurally, the ring also includes an active carboxyloxygen atom, a carbonyl carbon atom, an alpha carbon atom, and an alpha nitrogen atom, with adjacent atoms bound by coordinate covalent bonding. The structure of ferrous bis-glycinate chelate is described in more detail in Ashmead, H. DeWayne, "*Comparative Intestinal Absorption and Subsequent Metabolism of Metal Amino Acid Chelates and Inorganic Metal Salts*", in Subramanian, K. S., et al., Biological and Trace Element Research, American Chemical Society, Washington D.C., pp. 306-319, 1991, the disclosure of which is herein incorporated by reference in its entirety.

One form of ferrous bis-glycinate chelate is commercially available from Albion Laboratories Incorporated of Clearfield, Utah, and sold under the trade name Ferrochel®. Ferrochel® is a free flowing, fine granular powder that provides a high bioavailable source of ferrous iron that is typically complexed or chelated with the amino acid glycine. In one embodiment of the present invention, a combination of ferrous bis-glycinate chelate, such as Ferrochel®, and ferrous fumarate is formulated in a multivitamin/multimineral supplement for delivering elemental iron to pregnant or lactating women. Ferrous bis-glycinate chelate is also a stable form of iron. In addition, data from human and animal studies indicate that the ferrous bis-glycinate chelate is more readily bioavailable with fewer side effects than more commonly used iron salts, such as ferrous sulphate. Commercially available Ferrochel® may also contain iron-glycine chelation complexes other than the structure of ferrous bis-glycinate chelate described above, but in minute quantities.

Following ingestion, metal salts are generally ionized in the stomach upon exposure to the acidic gastric juices to form metal-cations and salt-anions depending on the particular metal, as described in Ashmead, H. DeWayne, *Comparative Intestinal Absorption and Subsequent Metabolism of Metal Amino Acid Chelates and Inorganic Metal Salts*, in Subramanian, K. S., et al., Biological Trace Element Research, American Chemical Society, Washington, D.C., pp. 306-319, 1991, the disclosure of which is herein incorporated by reference in its entirety. Assuming that no interfering chemical reactions occur, the cations enter the small intestine and typically bind to carrier proteins embedded in the lumigal membrane of the mucosal cells and are transported into the interior of the mucosal cell. The metals, also generally referred to as minerals, enter the cell either by active transport or by passive diffusion. This absorption can occur anywhere in the small intestine, but generally starts in the duodenum where solubility of the metal ion in the intestinal fluid improves due to a mildly acidic pH of the fluid (pH of about 5-6). Absorption is optimal in the upper jejunum where solubility is even greater in fluid having a mildly basic pH of about 7-8.

In the case of a metal-amino acid chelate, the metal ion, such as iron, in the chelate is chemically inert due to the coordinate covalent bonding of the amino acid ligands as described above. To this end, absorption of the chelate is not affected by precipitating salt-anions and free metal-cations as is the case with soluble metal salts. Furthermore, fats and fibers do not interfere with the absorption of the chelate due to the high formation constant (or the low dissociation constant). Thus, the iron uptake into circulation is increased by the use of an iron-amino acid chelate in accordance with the present invention. To this end, compositions including an iron-amino acid chelate, such as ferrous bis-glycinate chelate, provide increased bioavailability of the iron into the blood thereby providing greater efficiency in supplementing iron in a diet.

Besides the neutral state of a metal in a chelate, stability of the chelate is also a factor affecting bioavailability of the metal. Particularly, stability of the chelate to digestive enzymes and acid in the stomach plays a key role in bioavailability. To enhance stability in the digestive tract, it is advantageous for the chelate to have one or only a few amino acids forming a low molecular weight chelate, rather than having a multitude of amino acids forming a high molecular weight chelate. Beneficial low molecular weight chelates should have a total molecular weight, including the metal, of less than 1500. Low molecular weight metal-amino acid chelates, and particularly iron-amino acid chelates, are generally sufficiently stable and structurally survive enzymes and other elements of the digestive process. Moreover, smaller sized chelates generally resemble many of the characteristics of a dipeptide in terms of their stability properties. Ferrous bis-glycinate chelate, having only two glycine ligands bound to a single iron atom, is a suitable low molecular weight chelate. Without alteration in chemical structure during digestion, the ferrous bis-glycinate chelate can easily travel through the intestine, as would a dipeptide-like molecule. In addition, its relatively lower molecular weight facilitates the absorption of the chelate as an intact molecule, similar to that of a dipeptide molecule.

A high molecular weight metal-amino acid chelate, resulting from large molecular weight ligands such as polypeptides or proteins, has less chance of survival in the digestive tract. When a metal is "sequestered" in a chelate having a large, structural mass and a large molecular weight, the chelate may not be able to transport the metal ion through the mucosal membrane due to hydrolysis in the intestinal lumen. More specifically, increased hydrolysis of the amino acid polypeptide or protein ligands occur in the intestinal lumen leaving more free carboxylic acid and free amine fragments, rendering the chelate more hydrophilic and, therefore, more difficult to absorb. In addition, hydrolyzing enzymes may also break the links between the metal and the ligand further decreasing the ability of the chelate to transport the sequestered metal through the intestinal wall. The resulting free metal cation is subject to all the chemical reactions interfering with the absorption of the metal through the intestine.

Another reason that metal-amino acid chelates are a more bioavailable form of a metal than typical metal salts is because the structural complex of the chelate is generally capable of resisting the acidic pH of the stomach and surviving the digestive process better than commonly used metal salts. For example, the covalent complex of an iron-amino acid chelate is able to better resist the action of peptidases in the stomach, preventing breakage of internal peptide links and ionic associations between the ligand and iron atom, than most iron salts. To this end, an iron-amino acid chelate is less likely to be chemically degraded by the acidity in the stomach than other forms of iron. Moreover, a high stability constant for the iron-amino acid chelate also contributes to the bioavailability of the iron. Consequently, an intact metal-amino acid chelate is generally better absorbed through the intestinal membranes, thereby rendering the metal more bioavailable to the body, than less absorbed metal forms, as described in Ashmead, H. DeWayne, *Comparative Intestinal Absorption and Subsequent Metabolism of Metal Amino Acid Chelates and Inorganic Metal Salts.*

Iron-amino acid chelates, such as ferrous bis-glycinate chelate, may be used as the sole source of iron in the composition for supplementing dietary iron. However, it may also be combined with other bioavailable forms of iron. Alternate forms of bioavailabile iron include, without limitation, pharmaceutically acceptable salts. The term "pharmaceutically acceptable salts", as used herein, is intended to include all possible salt forms of iron that are government approved and, therefore, safe for ingestion. The term "salt", as used herein, is intended to refer to an ionic association of one or more charged species, either acids or bases, to one or more molecules of iron. Examples of suitable pharmaceutically acceptable salts of iron include, without limitation, ferric salts and ferrous salts. Examples of ferrous salts include, without limitation, ferrous fumarate, ferrous sulfate, ferrous succinate, ferrous gluconate, ferrous lactate, ferrous tartrate, and ferrous citrate. In one aspect of the present invention, the iron amino-acid chelate is combined with ferrous fumarate in a pharmaceutically acceptable dosage formulation for iron supplementation to mammals.

Ferrous fumarate ($C_4H_2FeO_4$) is the fumaric acid salt of elemental iron. More specifically, the carboxyl groups of both acids of a single fumaric acid molecule form a bi-dentate coordinate structure with iron to result in a stable, bioavailable iron salt having an iron:fumaric acid mole ratio or 1:1. Ferrous fumarate is a relatively concentrated form of iron (33% by weight is elemental iron) and, therefore, may be used in a dietary supplement to treat and prevent iron deficiencies in the body and particularly, iron deficiency anemia in pregnant females. Ferrous fumarate may be prepared by conventional methods known in the art. For example, one method of preparing ferrous fumarate is by combining hot aqueous solutions of ferrous sulfate and sodium fumarate, both of which are commercially available, and filtering the ferrous fumarate formed from the resulting slurry for separation thereof.

Where ferrous bis-glycinate chelate is used as the sole source of iron in the composition, a certain weight of the chelate would be needed to provide the recommended daily allowance of iron, particularly for a female during pregnancy and lactation. The amount of each form of iron will generally affect the overall size of the resulting tablet or other dosage form. In order to properly supplement dietary iron to the recommended daily allowance of about 3 mg, a once-a-day dosage of at least about 20 mg of elemental iron is generally needed. Ferrous bis-glycinate chelate is approximately 20% elemental iron by weight. Therefore, to obtain an equivalent dose of 20 mg of elemental iron, 100 mg of ferrous bis-glycinate chelate would need to be consumed. However, many pharmaceutically acceptable salt forms of elemental iron are often more concentrated in iron than a chelate and, therefore, would be required in smaller amounts to obtain the equivalent dose. For example, ferrous fumarate is approximately 33% elemental iron by weight. Therefore, to obtain a dose of 20 mg of elemental iron, about 60.6 mg of ferrous fumarate would need to be consumed, thereby resulting in a reduction in the size of the tablet. However, the improved oral bioavailability of the iron-amino acid chelate relative that of the pharmaceutically acceptable salt form offsets some of the concentration benefits of the salt form. Thus, a combination of an iron-amino acid chelate, such as Ferrochel®, with a second bioavailable form of elemental iron, such as ferrous fumarate, provides advantages related to the size of the supplement and ultimately to compliance with a dosage regimen.

In one embodiment of the present invention, the composition includes iron having a total weight sufficient for proper dietary supplementation in accordance with recommended dosages. In another embodiment, the composition includes iron having a total weight in a range from about 5 mg to about 200 mg. The iron may be provided completely as an iron-amino acid chelate or in combination with one or more iron salts. In another embodiment, the composition includes an iron-amino acid chelate in an amount sufficient to provide at least about 25% of the total weight of the iron in the composition. In yet another embodiment, the iron-amino acid chelate provides at least about 75% of the total weight, and in yet a further embodiment, it provides at least about 90% of the total weight of iron. In still a further embodiment, the iron-amino acid chelate contains about 25% to about 75% of the total weight of the iron in the composition, with the remaining iron contained in an alternate form of iron. In yet another embodiment, the iron-amino acid chelate contains about 25% to about 90% of the total weight of the iron in the composition, with the remaining iron contained as ferrous fumarate. Further embodiments include a combination of ferrous bis-glycinate chelate and ferrous fumarate as the bioavailable forms of iron. In one further embodiment, the ferrous fumarate contains about 75% and ferrous bis-glycinate chelate contains about 25% of the total weight of the iron present in the composition.

Where the composition includes a combination of forms of iron, i.e., an iron-amino acid chelate with another form of iron, the weights of each form are considered in providing the total weight of the iron for a reasonably sized composition. In one embodiment of the present invention, the composition includes the iron-amino acid chelate in a range from about 10 mg to about 200 mg. For a pregnant or lactating female, the composition may be a prenatal supplementary composition including about 69 mg of ferrous fumarate, which is about 22 mg of free elemental iron, and about 37 mg of ferrous bis-glycinate chelate, which is about 7.2 mg of elemental iron. Such a composition has a weight ratio of ferrous fumarate to ferrous bis-glycinate chelate of about 2-3:1 for providing bioavailable iron to the female. Altering the amounts of the iron-amino acid chelate with other forms of iron balances the benefits between the final size of the composition and the total amount of iron included therein, while providing an iron dose sufficient to be ingested once a day and meet the daily requirements of iron.

While the present composition includes one or more bioavailable forms of iron, the composition may further include vitamins and minerals, or pharmaceutically acceptable forms thereof, for administration as a vitamin/mineral supplement. In one aspect of the present invention, the composition includes multiple vitamins and multiple minerals and may be administered as a multivitamin/multimineral supplement. The term "pharmaceutically acceptable", as used herein with reference to a vitamin or a mineral, generally refers to all biologically acceptable forms of the vitamin and mineral, such as salt forms. The term "biologically acceptable" generally refers to a form safe for mammalian consumption. Vitamins and minerals, in general, are desirable for health reasons. Examples of suitable vitamins and minerals are listed below along with their health benefits. Without limitation, exemplary vitamins include vitamin A, vitamin B complex vitamins, vitamin C, vitamin D, vitamin E, and vitamin K.

When vitamin A is present in the composition, it is present in a range of about 0.002 mg to about 15 mg, or in a range of about 1 IU to about 7500 IU in a single dosage form. The generally accepted conversion rate of vitamin A is about 500,000 IU per gram. In one embodiment of the present invention vitamin A is beta-carotene present in about 8 mg to about 9 mg.

Non-limiting exemplary vitamin B complex vitamins include thiamine ($B_1$), riboflavin ($B_2$), niacin (niacinamide), pyridoxine ($B_6$), cyanocobalamin ($B_{12}$), biotin, pantothenic acid, folic acid, inositol or combinations thereof. Vitamin $B_1$, or thiamine, is essential for growth and the prevention of beriberi. When vitamin $B_1$ is present in the composition, it is present in a range of about 0.5 mg to about 50 mg in a single dosage form. In one embodiment, the vitamin $B_1$ is a monohydrate or mononitrate and present in a range of about 2.0 mg to about 2.5 mg.

Vitamin $B_2$, or riboflavin, is known to promote growth, particularly by functioning as a flavoprotein in tissue respiration. When vitamin $B_2$ is present in the composition, it is present in a range of about 0.5 mg to about 50 mg in a single dosage form. In one embodiment, the vitamin $B_2$ is present in a range of about 4.5 mg to about 5.5 mg.

Vitamin $B_6$, or pyridoxine, is believed to be helpful for fat metabolism, for dehydration and desulfhydration of amino acids, and for normal trypsin metabolism. Vitamin $B_6$ is also known to be useful for the treatment of nausea. When vitamin $B_6$ is present in the composition, it is present in a range of about 0.1 mg to about 200 mg in a single dosage form. In one embodiment, the vitamin $B_6$ is the HCl salt of pyridoxine and present in the composition in a range of about 40 mg to about 45 mg.

Vitamin $B_{12}$, or one of the three active forms, i.e., cyanocobalamin, hydroxocobalamin, and nitrocobalamin, is believed to influence nucleic acid synthesis, fat metabolism, conversion of carbohydrate to fat, and metabolism of glycine, serine, methionine, and choline. When vitamin $B_{12}$ is present in the composition, it is present in a range of about 2 mcg to about 250 mcg in a single dosage form. In one embodiment, the vitamin $B_{12}$ is present as 1% spray dried on starch and in a range of about 1.2 mg to about 1.7 mg.

Niacin (nicotinic acid) or its amide form, niacinamide, is believed necessary, along with other vitamins, for the prevention and cure of pellagra in humans. In addition, it functions in protein and carbohydrate metabolism. When niacinamide is present in the composition, it is present in a range of about 1 mg to about 100 mg in a single dosage form.

Folic acid has many known advantages and may be included in the composition. Particularly, folic acid is useful for the prevention of neural tube defects, particularly in a developing fetus. In one embodiment of the present invention, it is included in a range of about 0.01 mg to about 5 mg in a single dosage form. In another embodiment, folic acid is present in the composition in combination with an iron-amino acid chelate, such as ferrous bis-glycinate chelate, to form a supplement for treating anemia in a pregnant female. Ferrous bis-glycinate chelate and folic acid are useful for administration to a pregnant female in the third trimester of the pregnancy when anemia and anemia related symptoms generally are dangerous to both the expectant mother and the fetus. In yet another embodiment, the supplement includes about 80 mg of Ferrochel® combined with about 1 mg of folic acid in the form of a tablet for supplementing iron in pregnant females.

Vitamin C is known to be essential for the prevention of scurvy in humans. It also increases resistance to infections. When vitamin C is present in the composition, it is present in a range of about 10 mg to about 1000 mg in a single dosage form. In one embodiment, the vitamin C (ascorbic acid) or the pharmaceutically acceptable salt thereof, such as calcium ascorbate and sodium ascorbate, is present in about 130 mg to about 160 mg.

When vitamin D is present in the composition, it is present in a range of about 0.001 mg to about 0.6 mg in a single dosage form. Suitable D vitamins include, for example, vitamin $D_3$ (cholecalciferol) present in range above, or in a range of about 1 IU to about 600 IU wherein the conversion rate of vitamin $D_3$ is about 1,000,000 IU per gram.

When vitamin E is present in the composition, it is present in a range of about 1 mg to about 125 mg in a single dosage form. In one embodiment, the vitamin E (tocopherols) is a mixture of different tocopherols or the same tocopherol, such as di-alpha tocopheryl acetate, and present in the range above, or in a range of about 1 IU to about 100 IU wherein the conversion rate of vitamin E is about 800 IU per gram. In another embodiment, mixed tocopherols are present in about 45 mg in a single dosage of the composition.

Minerals that may be included in the present compositions are non-iron minerals. Non-limiting exemplary non-iron minerals include calcium, copper, zinc, magnesium, or their pharmaceutically accepted salts. Calcium is useful in the development of bones. When calcium is present in the composition, it is present in a range of about 20 mg to about 1000 mg in a single dosage form. In one embodiment, the calcium is a pharmaceutically acceptable form, such as calcium carbonate, and present in a range of about 80 mg to about 110 mg.

When copper is present in the composition, it is present in a range of about 0.1 mg to about 10 mg in a single dosage form. In one embodiment, the copper is a pharmaceutically acceptable form, such as cupric oxide, and present in a range of about 2.3 mg to about 3.0 mg.

When zinc is present in the composition, it is present in a range of about 5 mg to about 100 mg in a single dosage form. In one embodiment, the zinc is a pharmaceutically acceptable form, such as zinc oxide, and present in a range of about 30 mg to about 35 mg.

When magnesium is present in the composition, it is present in a range of 0.1 mg to about 400 mg in a single dosage form. Biologically acceptable forms of magnesium, such as magnesium oxide, are suitable for the compositions of the present invention.

In one exemplary embodiment, the multivitamin/multimineral supplement of the present invention contains iron in two bioavailable forms, an iron-amino acid chelate and a pharmaceutically acceptable salt form of iron, in combination with additional vitamins and minerals in the following ranges: vitamin A in the range of 0 IU to about 6,500 IU; vitamin $B_1$ in the range of about 0.5 mg to about 50 mg; vitamin $B_2$ in the range of about 0.5 mg to about 50 mg; vitamin $B_6$ being present in the range of about 0.1 mg to about 200 mg; vitamin $B_{12}$ being present in the range of about 2 mcg to about 250 mcg; niacinamide in the range of about 1 mg to about 100 mg; folic acid in the range of about 0.1 mg to about 5 mg; vitamin C in the range of about 10 mg to about 1000 mg; vitamin D in the range of about 1 IU to about 600 IU; vitamin E in the range of about 1 mg to about 100 mg; calcium in the range of about 20 mg to about 2000 mg; copper in the range of 0 mg to about 10 mg; zinc in the range of about 5 mg to about 100 mg; and magnesium in the range of 0 mg to about 400 mg.

In another exemplary embodiment, the multivitamin/multimineral supplement includes the following ingredients in the amounts shown in table 1.

TABLE 1

| | Amount |
|---|---|
| Vitamins | |
| A (beta carotene) | 3,000 IU |
| D (cholecalciferol) | 400 IU |
| E (provided by di-alpha tocopheryl acetate) | 30 mg |
| C (ascorbic acid, sodium ascorbate) | 120 mg |
| Folic acid | 1 mg |
| $B_1$ (thiamine mononitrate) | 1.8 mg |
| $B_2$ (riboflavin) | 4 mg |
| Niacinamide | 20 mg |
| $B_6$ (pyridoxine hydrochloride) | 25 mg |
| $B_{12}$ (cyanocobalamin) | 12 mcg |
| Minerals | |
| Calcium (calcium carbonate) | 100 mg |
| Copper (cupric oxide) | 2 mg |
| Iron (ferrous fumarate, ferrous bis-glycinate chelate) | 29 mg |
| Zinc (zinc oxide) | 25 mg |
| Magnesium (magnesium oxide) | 25 mg |

In yet another embodiment, the multivitamin/multimineral supplement includes the following ingredients in the amounts shown in Table 2.

TABLE 2

| | Amount |
|---|---|
| Vitamins | |
| A (beta carotene) | 3,000 IU |
| D (cholecalciferol) | 400 IU |
| E (di-alpha tocopheryl acetate) | 30 mg |
| C (ascorbic acid) | 120 mg |
| Folic acid | 1 mg |
| $B_1$ (thiamine mononitrate) | 1.8 mg |
| $B_2$ (riboflavin) | 4 mg |
| Niacinamide | 20 mg |
| $B_6$ (pyridoxine hydrochloride) | 25 mg |
| $B_{12}$ (cyanocobalamin) | 12 mcg |
| Minerals | |
| Calcium (calcium carbonate) | 200 mg |
| Copper (cupric oxide) | 2 mg |
| Iron (ferrous fumarate, ferrous bis-glycinate chelate) | 29 mg |
| Zinc | 25 mg |
| Magnesium (magnesium oxide) | 25 mg |

In the embodiments tabulated above, the 29 mg of elemental iron included in the composition may be provided in the form of 1-99% of ferrous fumarate and 1-99% of ferrous bis-glycinate chelate. Additionally, in either or both compositions, the ferrous bis-glycinate chelate may be provided by Ferrochel®.

In one embodiment of the present invention, the composition includes additives such as, for example, starches, saccharides, fats, antioxidants, amino acids, proteins, and derivatives or combinations thereof. Antioxidants generally improve the stability of the final composition. Additives used to formulate the final composition may also be included. For example, formulation additives such as natural oils, cellulose polymers, flavors, xylitol, corn starch, aspartame, acacia, sucrose, gelatin, citric acid, FB & C yellow #6, FD & C red #40, and flow agents may be included in the present composition as discussed herein below.

Additives included in the final dosage form of the composition, such as a tablet, are commonly referred to as excipients. Excipients provide physical or aesthetic properties to the dosage form for delivery of a compound or composition to the desired target location. For example, with respect to physical properties, tablets generally may need to have acceptable hardness, disintegration and dissolution rates for release of the therapeutic composition, as well as stability and size for effective delivery of the composition. With respect to aesthetics, the tablet may include additives that appeal to the senses, such as colorants, fragrances, texture modifiers, and/or flavoring agents.

By way of example, one or more lubricants may be added to the composition to assist in formulation by inhibiting sticking of the ingredients during compression of a pill or a tablet. Examples of suitable lubricants include, but are not limited to, stearic acid, palmitostearate, talc, and oils. Natural oils may be present as lubricants in the composition. Additionally, flavoring agents may be added to the composition. Flavoring agents include, for example, fruit flavors, or sweeteners, such as sodium saccharin, aspartame, confectionary sugar, sorbitol, sucrose, xylitol, or combinations thereof. Further, the composition may include disintegrants which are used to facilitate the breakup of the tablet after the tablet is administered to a patient. Examples of disintegrants include, but are not limited to, modified or unmodified starches such as corn starch, potato starch, or wheat starch or sodium croscarmellose. Additionally, suitable colorants, such as red beet powder, ferric oxides, FD & C dyes or combinations thereof, may be used in the present compositions. More specifically, the composition may include FD & C yellow #6, and FD & C red #40 for example.

In accordance with one aspect of the present invention, the composition of the present invention is formulated into single dosage forms suitable for ingestion. Without limitation, exemplary dosage forms include pills, tablets, caplets, and capsules, made by processes known in the art of pharmaceutical manufacturing. Generally, capsules may be formed by blending the constituents, including the forms of iron, vitamins and other minerals, and subsequently filling capsules with the mixture using conventional automatic filling equipment. Examples of capsules include, without limitation, soft gelatin capsules and hard gelatin capsules. The capsules may be prepared by methods well known to persons of ordinary skill in the art. For example, a soft gel or soft gelatin capsule may be prepared by dispersing the formulation in an appropriate vehicle (vegetable oils are commonly used) to form a high viscosity mixture. This mixture is then encapsulated with a gelatin-based film using technology and machinery known to those in the soft gel industry. The industrial units so formed are then dried to a constant weight.

Tablet compositions are commonly used to deliver therapeutic compounds to a patient such as a human or an animal. The term "tablet", as used herein, is meant to refer to a solid particle, containing or including compounds that are compressed under pressure into any shape. In one embodiment of the present invention, the final composition is formulated into a tablet. Examples of suitable tablet forms include, without limitation, chewable tablets, quick dissolve tablets, effervescent tablets, multi-layer tablets, and bi-layer tablets. Tablets are convenient and may be produced using conventional techniques.

To produce a tablet, the composition is typically formed into a compactable granular mixture. One skilled in the art will recognize that there are various ways to form a compactable granular mixture. Conventional methods of combining the components of the composition and other desired additives to form a compactable granular mixture may be used. For example, a compactable granular mixture may be formed by first blending the iron-amino acid chelate, and other forms of iron if desired, with desired vitamins, additional minerals and suitable excipients to form a dry blend. Alternatively, the desired components of the composition may be partially or completely dissolved in a suitable liquid, after which the liquid is removed to form a compactable granular mixture. Persons of ordinary skilled in the art readily appreciate that the desired method chosen for forming the compactable granular mixture will depend on many factors including, for example, the selection of the specific forms of iron, vitamins, minerals, and additives for the composition.

The compactable granular mixture may then be further processed using conventional techniques to form the final tablet. For example, a compactable granular mixture may be compressed into a tablet according to any technique known to those skilled in the art, such as placing the compactible granular mixture into a die and compressing the mixture into a tablet having the desired shape and weight. The application of an external lubricant to the wall of the die prior to adding the granular mixture to the die is generally helpful. Further, the mixture may be compressed at a pressure and temperature suitable to form a tablet having the desired properties such as strength, hardness, disintegration, and release of the therapeutic compounds of the composition upon administration. In one embodiment, the tablet is soft and chewable. Depending upon the amount of iron included in the composition, a chewable form of a tablet would otherwise overcome difficulties in swallowing a hard, solid tablet. This is especially true for children and adults having small oral and pharyngeal cavities. In any event, the compaction conditions should be such that there is minimal, if any, degradation of the therapeutic compounds of the composition. In addition, the compaction conditions should be performed at below the melting points of the therapeutic compounds of the composition to prevent a reduction in tablet hardness and to reduce or eliminate other tablet-making process problems, such as glazing for example.

The tablets produced may be further processed as desired. For example, the tablet may be coated by a technique known to those skilled in the art. Coating the single dosage formulation provides the benefits of delaying or sustaining the release of the ingredients in the composition. Coatings further reduce or minimize degradation and clearance of the composition prior to absorption. For example, specific coatings are designed to optimize survival of the composition in the stomach while other coatings are designed to prevent gastro-intestinal tract upset. Particularly, enteric coatings provide useful advantages. Particularly, enteric coatings are known for the ability to resist acidic pH of the stomach and readily dissolve as the pH of the surrounding media increases into the range of about 4-8, which is generally found in the duodenum and upper jejunum of the small intestine. Accordingly, enteric coatings enhance absorption and bioavailability. Further, coatings generally provide a cohesive, compact film around the composition for resistance to permeation of moisture and water vapor into the composition. Moreover, coatings in general, and enteric coatings in particular, provide this barrier with a minimal increase in weight of the composition (about 6-8% for an Opadry® enteric coating system) depending upon overall size of the composition. Suitable coatings generally comprise polymers in combination with an excipient, such as a plasticizer, and/or in combination with a colorant, such as a pigment.

The present invention also provides methods of supplementing iron in a mammal by administering the compositions described above to the mammal. The composition is advantageously formulated into a single dosage form as described above for administration to the mammal. In one embodiment of the present invention, the formulation is enterically coated for providing sustained release characteristics to the single dosage form. The dosage form may be a prenatal supplement for administration to a pregnant and lactating female or a general supplement available for self-administration.

By virtue of the foregoing, there are provided compositions and methods for supplementing iron in the diet. The compositions include a highly bioavailable form of iron in an iron-amino acid chelate, such as ferrous bis-glycinate chelate, and may further include a bioavailable salt form of iron, such as ferrous fumarate. The present compositions may further serve as multivitamin/multimineral dietary supplements by inclusion of additional vitamins and minerals. A combination of the two forms of iron above provides a balance between the oral bioavailability of the iron and the size of the composition, and does so without producing undesirable gastrointestinal side effects following ingestion. The present invention is useful for supplementing iron in mammals having iron deficient diets, and in particular, in pregnant and lactating females suffering from anemia. Smaller dosage forms, such as tablets and capsules for example, that are easier to swallow than the otherwise relatively large prior art prenatal vitamin or dietary supplements are more likely to be ingested in compliance with a regimen.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. For example, as other bioavailable forms of an iron-amino acid chelate become apparent and to those skilled in the art, the present invention may be include such forms, and not be limited to the forms listed herein. Therefore, the invention in its broader aspects is not limited to the specific details, methods and examples described. Accordingly, departures may be made from such details without departure from the spirit or scope of applicant's general inventive concept.

What is claimed is:

1. A composition suitable for administration to a pregnant or lactating female, the composition consisting of:
    bioavailable iron in a form of at least one iron-amino acid chelate and a pharmaceutically acceptable salt;
    a combination of vitamins or pharmaceutically acceptable salts thereof, the combination consisting of:
        vitamin A in a weight of up to about 15 mg;
        vitamin B1 in a weight range from about 0.5 mg to about 50 mg;
        vitamin B2 in a weight range from about 0.5 mg to about 50 mg;
        vitamin B6 in a weight range from about 0.1 mg to about 200 mg;
        vitamin B12 in a weight range from about 2 mcg to about 250 mcg;
        niacinamide in a weight range from about 1 mg to about 100 mg;
        folic acid in a weight range from about 0.01 mg to about 5 mg;
        vitamin C in a weight range from about 10 mg to about 1000 mg;
        vitamin D in a weight range from about 0.001 mg to about 0.6 mg; and
        vitamin E in a weight range from about 1 mg to about 125 mg;
    a combination of minerals or pharmaceutically acceptable salts thereof, the combination consisting of:
        calcium in a weight range from about 10 mg to about 2000 mg;
        copper in a weight of up to about 10 mg;
        zinc in a weight range from about 5 mg to about 100 mg; and
        magnesium in a weight of up to about 400 mg; and
    excipients that provide physical properties to the composition and allow delivery of the composition to a pregnant or lactating female as a pill, a tablet, a caplet, or a capsule.

2. The composition of claim 1 wherein the iron-amino acid chelate consists of an iron chelated to at least one amino acid.

3. The composition of claim 2 wherein the at least one amino acid is selected from the group consisting of alanine, arginine, asparagine, aspartic acid, cysteine, cystine, glutamine, glutamic acid, glycine, histidine, hydroxyproline, isoleucine, lysine, leucine, methionine, ornithine, phenylalanine, proline, serine, threonine, tryptophan, tyrosine, valine, and combinations thereof.

4. The composition of claim 1 wherein the iron-amino acid chelate is ferrous bis-glycinate chelate.

5. The composition of claim 1 wherein the pharmaceutically acceptable salt form of iron is selected from the group consisting of ferrous fumarate, ferrous sulfate, ferrous succinate, ferrous gluconate, ferrous lactate, ferrous tartarate, ferrous citrate, and combinations thereof.

6. The composition of claim 1 wherein the iron has a total weight in a range from about 5 mg to about 200 mg in the composition.

7. The composition of claim 6 wherein the pharmaceutically acceptable salt form of iron is from about 25% to about 75% of the total weight of the iron in the composition.

8. The composition of claim 6 wherein the iron-amino acid chelate is at least about 25% of the total weight of the iron in the composition.

9. The composition of claim 6 wherein the iron-amino acid chelate is at least about 75% of the total weight of the iron in the composition.

10. The composition of claim 1 wherein the iron-amino acid chelate is at least about 90% of the total weight of the iron in the composition.

11. A multivitamin/multimineral supplement suitable for administration to a pregnant or lactating female, the multivitamin/multimineral supplement consisting of:
    bioavailable iron in a form consisting of at least one iron-amino acid chelate and a pharmaceutically acceptable salt; and
    a multivitamin/multimineral component consisting of:
        a combination of vitamins or pharmaceutically acceptable salts thereof, the combination consisting of:
            vitamin A in a weight of up to about 15 mg;
            vitamin B1 in a weight range from about 0.5 mg to about 50 mg;
            vitamin B2 in a weight range from about 0.5 mg to about 50 mg;
            vitamin B6 in a weight range from about 0.1 mg to about 200 mg;
            vitamin B12 in a weight range from about 2 mcg to about 250 mcg;
            niacinamide in a weight range from about 1 mg to about 100 mg;
            folic acid in a weight range from about 0.01 mg to about 5 mg;
            vitamin C in a weight range from about 10 mg to about 1000 mg;
            vitamin D in a weight range from about 0.001 mg to about 0.6 mg; and
            vitamin E in a weight range from about 1 mg to about 125 mg; and a combination of minerals or pharmaceutically acceptable salts thereof, the combination consisting of:
  calcium in a weight range from about 10 mg to about 2000 mg;
  copper in a weight of up to about 10 mg;
  zinc in a weight range from about 5 mg to about 100 mg; and
  magnesium in a weight of up to about 400 mg; and
wherein the supplement is in a single dosage formulation selected from the group consisting of a pill, a tablet, a caplet, and a capsule.

12. The supplement of claim 11 wherein the iron-amino acid chelate consists of at least one molecule of iron chelated to at least one amino acid.

13. The supplement of claim 11 wherein the iron-amino acid chelate is ferrous bis-glycinate chelate.

14. The supplement of claim 11 wherein the iron-amino acid chelate has a weight in the range from about 10 mg to about 200 mg.

15. The supplement of claim 11 wherein the pharmaceutically acceptable salt form of iron is selected from the group consisting of ferrous fumarate, ferrous sulfate, ferrous succinate, ferrous gluconate, ferrous lactate, ferrous tartarate, ferrous citrate, and combinations thereof.

16. The supplement of claim 11 wherein the pharmaceutically acceptable salt form of iron has a weight in the range from about 10 to about 200 mg.

17. The supplement of claim 16 wherein the pharmaceutically acceptable salt form of iron is ferrous fumarate.

18. The supplement of claim 11 wherein the iron is in an amount that allows the supplement to be administered once-a-day.

19. A method for supplementing iron to a pregnant or lactating female, the method comprising administering to the pregnant or lactating female a composition consisting of:
  bioavailable iron in a form of at least one iron-amino acid chelate and a pharmaceutically acceptable salt in combination with multivitamins and multiminerals; and
  excipients that provide physical properties to the composition and allow delivery of the composition to a human as a pill, a tablet, a caplet, or a capsule; and
wherein the multivitamins and multiminerals consist of a combination of vitamins or pharmaceutically acceptable salts thereof consisting of:
  vitamin A in a weight of up to about 15 mg;
  vitamin B1 in a weight range from about 0.5 mg to about 50 mg;
  vitamin B2 in a weight range from about 0.5 mg to about 50 mg;
  vitamin B6 in a weight range from about 0.1 mg to about 200 mg;
  vitamin B12 in a weight range from about 2 mcg to about 250 mcg;
  niacinamide in a weight range from about 1 mg to about 100 mg;
  folic acid in a weight range from about 0.01 mg to about 5 mg;
  vitamin C in a weight range from about 10 mg to about 1000 mg;
  vitamin D in a weight range from about 0.001 mg to about 0.6 mg; and
  vitamin E in a weight range from about 1 mg to about 125 mg; and
a combination of minerals or pharmaceutically acceptable salts thereof consisting of:
  calcium in a weight range from about 10 mg to about 2000 mg;
  copper in a weight of up to about 10 mg;
  zinc in a weight range from about 5 mg to about 100 mg; and
  magnesium in a weight of up to about 400 mg.

20. The method of claim 19 wherein the iron-amino acid chelate administered consists of a molecule of iron chelated to at least one amino acid.

21. The method of claim 19 wherein the amino acid is selected from the group consisting of alanine, arginine, asparagine, aspartic acid, cysteine, cystine, glutamine, glutamic acid, glycine, histidine, hydroxyproline, isoleucine, lysine, leucine, methionine, ornithine, phenylalanine, proline, serine, threonine, tryptophan, tyrosine, valine, and combinations thereof.

22. The method of claim 19 wherein the iron-amino acid chelate is ferrous bis-glycinate chelate.

23. The method of claim 19 wherein the pharmaceutically acceptable salt form of iron is selected from the group consisting of ferrous fumarate, ferrous sulfate, ferrous succinate, ferrous gluconate, ferrous lactate, ferrous tartarate, ferrous citrate, and combinations thereof.

24. The method of claim 19 wherein the iron-amino acid chelate is:
  ferrous bis-glycinate chelate in a weight range from about 10 mg to about 200 mg; and
  wherein the pharmaceutically acceptable salt form of iron is ferrous fumarate in a weight range from about 10 mg to about 200 mg.

25. The method of claim 19 wherein the composition is administered for treating anemia in said female.

26. A method for supplementing iron in a pregnant or lactating female comprising administering a multivitamin/multimineral supplement to the pregnant or lactating female, in a pharmaceutically acceptable single dosage formulation chosen from a pill, a tablet, a caplet, and a capsule, the multivitamin/multimineral supplement consisting of:
  iron in a form consisting of at least one iron-amino acid chelate and a pharmaceutically acceptable salt;
  a combination of vitamins or pharmaceutically acceptable salts thereof consisting of:
    vitamin A in a weight of up to about 15 mg;
    vitamin B1 in a weight range from about 0.5 mg to about 50 mg;
    vitamin B2 in a weight range from about 0.5 mg to about 50 mg;
    vitamin B6 in a weight range from about 0.1 mg to about 200 mg;
    vitamin B12 in a weight range from about 2 mcg to about 250 mcg;
    niacinamide in a weight range from about 1 mg to about 100 mg;
    folic acid in a weight range from about 0.01 mg to about 5 mg;
    vitamin C in a weight range from about 10 mg to about 1000 mg;
    vitamin D in a weight range from about 0.001 mg to about 0.6 mg; and
    vitamin E in a weight range from about 1 mg to about 125 mg; and
  a combination of minerals or pharmaceutically acceptable salts thereof consisting of:
    calcium in a weight range from about 10 mg to about 2000 mg;
    copper in a weight of up to about 10 mg;
    zinc in a weight range from about 5 mg to about 100 mg; and
    magnesium in a weight of up to about 400 mg.

27. The method of claim 26 wherein the iron-amino acid chelate provides at least about 75% of the total weight of the iron in the administered supplement.

28. The method of claim 26 wherein the iron-amino acid chelate provides at least about 90% of the total weight of the iron in the administered supplement.

29. The method of claim 26 wherein the iron-amino acid chelate is ferrous bis-glycinate chelate in a weight range from about 10 mg to about 200 mg.

30. The method of claim 26 wherein the supplement is administered for the treatment of anemia.

31. A method for reducing iron deficiency in a pregnant or lactating female comprising administering to the pregnant or lactating female, in a pharmaceutically acceptable single dosage formulation chosen from a pill, a tablet, a caplet, and a capsule, a composition consisting of:
   bioavailable iron in a form of at least one iron-amino acid chelate and a pharmaceutically acceptable salt;
   a combination of vitamins or pharmaceutically acceptable salts thereof consisting of:
      vitamin A in a weight of up to about 15 mg;
      vitamin B1 in a weight range from about 0.5 mg to about 50 mg;
      vitamin B2 in a weight range from about 0.5 mg to about 50 mg;
      vitamin B6 in a weight range from about 0.1 mg to about 200 mg;
      vitamin B12 in a weight range from about 2 mcg to about 250 mcg;
      niacinamide in a weight range from about 1 mg to about 100 mg;
      folic acid in a weight range from about 0.01 mg to about 5 mg;
      vitamin C in a weight range from about 10 mg to about 1000 mg;
      vitamin D in a weight range from about 0.001 mg to about 0.6 mg; and
      vitamin E in a weight range from about 1 mg to about 125 mg; and
   a combination of minerals or pharmaceutically acceptable salts thereof consisting of:
      calcium in a weight range from about 10 mg to about 2000 mg;
      copper in a weight of up to about 10 mg;
      zinc in a weight range from about 5 mg to about 100 mg; and
      magnesium in a weight of up to about 400 mg.

32. The method of claim 31 wherein the iron-amino acid chelate is ferrous bis-glycinate chelate in a weight range from about 10 mg to about 200 mg.

33. The method of claim 31 wherein the folic acid has a weight in the range from about 0.01 mg to about 5 mg.

34. The method of claim 31 wherein the pregnant or lactating female is anemic.

35. A multivitamin, multimineral composition suitable for administration to a pregnant or lactating female consisting of:
   bioavailable iron in a form of at least one iron-amino acid chelate and a pharmaceutically acceptable salt;
   a combination of vitamins or pharmaceutically acceptable salts thereof consisting of:
      vitamin A in a weight of up to about 15 mg;
      vitamin B1 in a weight range from about 0.5 mg to about 50 mg;
      vitamin B2 in a weight range from about 0.5 mg to about 50 mg;
      vitamin B6 in a weight range from about 0.1 mg to about 200 mg;
      vitamin B12 in a weight range from about 2 mcg to about 250 mcg;
      niacinamide in a weight range from about 1 mg to about 100 mg;
      folic acid in a weight range from about 0.01 mg to about 5 mg;
      vitamin C in a weight range from about 10 mg to about 1000 mg;
      vitamin D in a weight range from about 0.001 mg to about 0.6 mg; and
      vitamin E in a weight range from about 1 mg to about 125 mg; and
   a combination of minerals or pharmaceutically acceptable salts thereof consisting of:
      calcium in a weight range from about 10 mg to about 2000 mg;
      copper in a weight of up to about 10 mg;
      zinc in a weight range from about 5 mg to about 100 mg; and
      magnesium in a weight of up to about 400 mg; and
   excipients that provide physical properties to the composition and allow delivery of the composition to a patient as a compressed tablet; and
   wherein said composition does not include any further vitamins or pharmaceutically acceptable salts thereof, and wherein said composition does not include any further minerals or pharmaceutically acceptable salts thereof.

36. A multivitamin, multimineral composition suitable for administration to a pregnant or lactating female consisting of:
   bioavailable iron in a form of at least one iron-amino acid chelate and a pharmaceutically acceptable salt;
   a combination of vitamins or pharmaceutically acceptable salts thereof consisting of:
      vitamin A in a weight of up to about 15 mg;
      vitamin B1 in a weight range from about 0.5 mg to about 50 mg;
      vitamin B2 in a weight range from about 0.5 mg to about 50 mg;
      vitamin B6 in a weight range from about 0.1 mg to about 200 mg;
      vitamin B12 in a weight range from about 2 mcg to about 250 mcg;
      niacinamide in a weight range from about 1 mg to about 100 mg;
      folic acid in a weight range from about 0.01 mg to about 5 mg;
      vitamin C in a weight range from about 10 mg to about 1000 mg;
      vitamin D in a weight range from about 0.001 mg to about 0.6 mg; and
      vitamin E in a weight range from about 1 mg to about 125 mg;
   a combination of minerals or pharmaceutically acceptable salts thereof consisting of:
      calcium in a weight range from about 10 mg to about 2000 mg;
      copper in a weight of up to about 10 mg;
      zinc in a weight range from about 5 mg to about 100 mg; and
      magnesium in a weight of up to about 400 mg;
   excipients that provide physical properties to the composition, the composition being in the form of a coated compressed tablet; and
   a disintegrant.

* * * * *

UNITED STATES PATENT AND TRADEMARK OFFICE
CERTIFICATE OF CORRECTION

PATENT NO.         : 7,994,217 B2                                     Page 1 of 1
APPLICATION NO.    : 10/375600
DATED              : August 9, 2011
INVENTOR(S)        : Prasad Nidamarty et al.

It is certified that error appears in the above-identified patent and that said Letters Patent is hereby corrected as shown below:

On the title page item (60),
Line approx. 28, add "Related U.S. Application Data"

On the title page item (30),
Line approx. 30, add "Provisional application No. 60/377,339, filed on May 5, 2002."

Title page item (56) under other Pub.
Page 1, Column 2,
Line approx. 36, "Coptin," should be --Coplin,--.
Line approx. 38, "Bioavallability" should be --Bioavailability--.

Title page item (56) under other Pub.
Page 2, Column 1,
Line approx. 9, "Reeiprolenting" should be --Repleting--.

Page 2, Column 2,
Line 8, "sulrface" should be --sulfate--.
Line 8, "dificiency" should be --deficiency--.

Column 7,
Line 42, "occur" should be --occurs--.

Column 8,
Line 28, "or" should be --of--.

Column 15,
Line 26, "applicant" should be --applicants--.
Line 31, "may be include" should be --may include--.
Line 36, "applicant's" should be --applicants'--.

Signed and Sealed this
First Day of November, 2011

David J. Kappos
*Director of the United States Patent and Trademark Office*